(12) United States Patent
Mottram et al.

(10) Patent No.: US 12,702,499 B2
(45) Date of Patent: Aug. 11, 2026

(54) CONTROL SYSTEM OF A SURGICAL ROBOT

(71) Applicant: CMR Surgical Limited, Cambridge (GB)

(72) Inventors: Edward John Mottram, Cambridge (GB); Graham John Veitch, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 315 days.

(21) Appl. No.: 17/995,238

(22) PCT Filed: Mar. 29, 2021

(86) PCT No.: PCT/GB2021/050765

§ 371 (c)(1),
(2) Date: Sep. 30, 2022

(87) PCT Pub. No.: WO2021/198661

PCT Pub. Date: Oct. 7, 2021

(65) Prior Publication Data

US 2023/0149101 A1 May 18, 2023

(30) Foreign Application Priority Data

Mar. 31, 2020 (GB) ...................................... 2004751

(51) Int. Cl.
*A61B 34/30* (2016.01)
*A61B 34/20* (2016.01)
*A61B 90/00* (2016.01)

(52) U.S. Cl.
CPC ...... *A61B 34/30* (2016.02); *A61B 2034/2059* (2016.02); *A61B 2090/066* (2016.02); *A61B 2090/067* (2016.02)

(58) Field of Classification Search
CPC ............ A61B 34/30; A61B 2034/2059; A61B 2090/066; A61B 2090/067;
(Continued)

(56) References Cited

U.S. PATENT DOCUMENTS 5,086,401 A 2/1992 Glassman et al.
5,184,601 A 2/1993 Putman
(Continued)

FOREIGN PATENT DOCUMENTS

CN 101106952 A 1/2008
CN 101227870 A 7/2008
(Continued)

OTHER PUBLICATIONS

Search Report dated Sep. 17, 2020, for GB Patent Application No. 2004752.8.
(Continued)

*Primary Examiner* — Shannon S Campbell
(74) *Attorney, Agent, or Firm* — Renner, Otto, Boisselle, & Sklar, LLP

(57) ABSTRACT

A control system of a surgical robot arm, the surgical robot arm comprising a series of joints by which the configuration of that surgical robot arm can be altered and one or more force or torque sensors, each force or torque sensor configured to sense a force or torque at a joint of the series of joints, the control system being configured to control the configuration of the surgical robot arm to be altered in response to an externally applied force or torque by: receiving sensory data from the one or more force or torque sensors indicative of a sensed force or torque at a part of the surgical robot arm resulting from the externally applied force or torque; determining a position of the part of the surgical robot arm using a reference position, whereby the sensed force or torque would be compensated by moving the
(Continued)

part of the surgical robot arm to the determined position; sending a command signal to the surgical robot arm to drive the part of the surgical robot arm to the determined position; and updating the reference position if the difference between the reference position and the determined position is greater than a threshold displacement.

20 Claims, 7 Drawing Sheets

(58) Field of Classification Search
CPC .............. A61B 2090/064; A61B 34/00; A61B 2034/301; B25J 9/1656; B25J 13/085; B25J 9/1694; G05B 19/423; G05B 2219/36429; G05B 2219/40599
See application file for complete search history.

(56) References Cited

U.S. PATENT DOCUMENTS

| | | | | |
|---|---|---|---|---|
| 6,233,504 | B1 | 5/2001 | Das et al. | |
| 6,436,107 | B1 | 8/2002 | Wang et al. | |
| 6,788,018 | B1 | 9/2004 | Blumenkranz | |
| 9,393,687 | B2 | 7/2016 | Hietmann et al. | |
| 9,724,827 | B2 | 8/2017 | Ueberle | |
| 9,855,662 | B2 | 1/2018 | Ruiz Morales et al. | |
| 9,943,964 | B2 | 4/2018 | Hares | |
| 9,968,405 | B2 | 5/2018 | Cooper et al. | |
| 10,016,900 | B1 | 7/2018 | Meyer et al. | |
| 10,272,569 | B2 | 4/2019 | Swarup et al. | |
| 10,405,944 | B2 | 9/2019 | Swarup et al. | |
| 11,707,337 | B2 | 7/2023 | Itkowitz et al. | |
| 2002/0120252 | A1 | 8/2002 | Brock et al. | |
| 2002/0120254 | A1 | 8/2002 | Julian et al. | |
| 2003/0055410 | A1 | 3/2003 | Evans et al. | |
| 2003/0097060 | A1 | 5/2003 | Yanof et al. | |
| 2005/0096502 | A1 | 5/2005 | Khalili | |
| 2006/0293643 | A1 | 12/2006 | Wallace et al. | |
| 2006/0293646 | A1 | 12/2006 | Whayne et al. | |
| 2007/0013336 | A1 | 1/2007 | Nowlin et al. | |
| 2007/0138992 | A1 | 6/2007 | Prisco et al. | |
| 2010/0160728 | A1 | 6/2010 | Yoshie | |
| 2011/0040305 | A1 | 2/2011 | Gomez et al. | |
| 2011/0130718 | A1 | 6/2011 | Kidd et al. | |
| 2012/0283747 | A1 | 11/2012 | Popovic | |
| 2013/0116706 | A1 | 5/2013 | Lee et al. | |
| 2014/0081461 | A1 * | 3/2014 | Williamson | B25J 9/1643 700/261 |
| 2014/0142592 | A1 | 5/2014 | Moon et al. | |
| 2014/0195052 | A1 | 7/2014 | Tsusaka et al. | |
| 2014/0200851 | A1 | 7/2014 | Weir et al. | |
| 2014/0222207 | A1 | 8/2014 | Bowling et al. | |
| 2014/0228862 | A1 | 8/2014 | Inoue et al. | |
| 2014/0358161 | A1 | 12/2014 | Hourtash et al. | |
| 2015/0202015 | A1 | 7/2015 | Elhawary et al. | |
| 2015/0282828 | A1 | 10/2015 | Kishi et al. | |
| 2015/0351857 | A1 | 12/2015 | Vander Poorten et al. | |
| 2016/0184032 | A1 | 6/2016 | Romo et al. | |
| 2016/0228203 | A1 | 8/2016 | Yamanaka et al. | |
| 2017/0128136 | A1 | 5/2017 | Post | |
| 2017/0143435 | A1 | 5/2017 | Scholan et al. | |
| 2017/0156806 | A1 | 6/2017 | Prisco et al. | |
| 2017/0165847 | A1 | 6/2017 | Popovic et al. | |
| 2017/0367774 | A1 | 12/2017 | Scholan | |
| 2018/0008359 | A1 * | 1/2018 | Randle | A61B 34/32 |
| 2018/0161115 | A1 | 6/2018 | Farritor et al. | |
| 2019/0053862 | A1 | 2/2019 | Ecke et al. | |
| 2019/0105117 | A1 | 4/2019 | Brisson | |
| 2019/0202066 | A1 | 7/2019 | Maret | |
| 2020/0039086 | A1 | 2/2020 | Meyer et al. | |
| 2021/0059766 | A1 | 3/2021 | Graetzel et al. | |
| 2021/0353381 | A1 | 11/2021 | Usui et al. | |
| 2022/0152820 | A1 * | 5/2022 | Spenninger | B25J 9/1633 |
| 2022/0388161 | A1 | 12/2022 | Spenninger et al. | |
| 2023/0063392 | A1 | 3/2023 | Farnioli | |
| 2023/0149101 | A1 | 5/2023 | Mottram et al. | |
| 2023/0172676 | A1 | 6/2023 | Mottram et al. | |

FOREIGN PATENT DOCUMENTS

| | | | |
|---|---|---|---|
| CN | 102327152 | A | 1/2012 |
| CN | 107072730 | A | 8/2017 |
| CN | 105616007 | B | 5/2019 |
| CN | 109758232 | A | 5/2019 |
| CN | 110559082 | A | 12/2019 |
| DE | 202019102430 | U1 | 6/2019 |
| EP | 1815950 | A1 | 8/2007 |
| GB | 2533004 | A | 6/2016 |
| GB | 2534558 | A | 8/2016 |
| GB | 2575113 | A | 1/2020 |
| JP | H05111889 | A | 5/1993 |
| JP | 2005329476 | A | 12/2005 |
| JP | 2010507792 | A | 3/2010 |
| JP | 2011517419 | A | 6/2011 |
| JP | 2013510632 | A | 3/2013 |
| JP | 2013132747 | A | 7/2013 |
| JP | 2015524309 | A | 8/2015 |
| JP | 2015163196 | A | 9/2015 |
| JP | 2015529163 | A | 10/2015 |
| JP | 2015530906 | A | 10/2015 |
| JP | 2016179168 | A | 10/2016 |
| JP | 2017512553 | A | 5/2017 |
| JP | 2017533795 | A | 11/2017 |
| JP | 2017538456 | A | 12/2017 |
| JP | 2018500095 | A | 1/2018 |
| JP | 2018524186 | A | 8/2018 |
| JP | 2019500925 | A | 1/2019 |
| JP | 6469304 | B1 | 2/2019 |
| JP | 2019022670 | A | 2/2019 |
| JP | 2019529051 | A | 10/2019 |
| JP | 2020536755 | A | 12/2020 |
| KR | 20110047929 | A | 5/2011 |
| KR | 20120014758 | A | 2/2012 |
| WO | 2000051486 | A1 | 9/2000 |
| WO | 2006124390 | A2 | 11/2006 |
| WO | 2009123891 | A1 | 10/2009 |
| WO | 2013116869 | A1 | 8/2013 |
| WO | 2014020571 | A1 | 2/2014 |
| WO | 2015142796 | A1 | 9/2015 |
| WO | 2016116753 | A1 | 7/2016 |
| WO | 2016152046 | A1 | 9/2016 |
| WO | 2017165183 | A1 | 9/2017 |
| WO | 2017221323 | A1 | 12/2017 |
| WO | 2019050821 | A1 | 3/2019 |
| WO | 2019074670 | A1 | 4/2019 |
| WO | 2019117896 | A1 | 6/2019 |
| WO | 2019204013 | A1 | 10/2019 |
| WO | 2020001742 | A1 | 1/2020 |

OTHER PUBLICATIONS

Search Report dated Sep. 17, 2020, for GB Patent Application No. 2004753.6.

International Search Report and Written Opinion mailed Jun. 15, 2021, for International Patent Application No. PCT/GB2021/050766.

International Search Report and Written Opinion mailed Jul. 1, 2021, for International Patent Application No. PCT/GB2021/050768.

Search Report dated Sep. 17, 2020, for priority GB Patent Application No. 2004751.0.

International Search Report and Written Opinion mailed Oct. 29, 2021, for priority International Patent Application No. PCT/GB2021/050765.

Search Report dated Jun. 15, 2015, for GB Patent Application No. 1501031.7.

International Search Report and Written Opinion mailed May 10, 2016, for International Patent Application No. PCT/GB2016/050125.

Non-Final Office Action dated Oct. 1, 2019, for U.S. Appl. No. 15/545,454.

(56) References Cited

OTHER PUBLICATIONS

Final Office Action dated Nov. 16, 2020, for U.S. Appl. No. 15/545,454.
Non-Final Office Action dated Dec. 17, 2020, for U.S. Appl. No. 16/880,547.
Final Office Action dated Apr. 30, 2021, for U.S. Appl. No. 16/880,547.
Non-Final Office Action dated Oct. 7, 2021, for U.S. Appl. No. 16/880,547.
Final Office Action dated Mar. 18, 2022, for U.S. Appl. No. 16/880,547.

* cited by examiner

CONTROL SYSTEM OF A SURGICAL ROBOT

This application is a national phase of International Patent Application No. PCT/GB2021/050765 filed Mar. 29, 2021, which claims priority to United Kingdom Patent Application No. 2004751.0 filed Mar. 31, 2020, each of which is hereby incorporated herein by reference in its entirety.

BACKGROUND

This invention relates to a control system of a surgical robot arm.

Invasive medical procedures can be performed using surgical robotic systems. FIG. 1 shows a typical surgical robotic system. The surgical robotic system 100 is shown performing an invasive medical procedure on a patient 102 positioned on an operating table 103. The surgical robotic system 100 comprises an arm 101. The arm 101 carries a surgical tool 106, such as a tool for performing cutting or grasping or an imaging device such as an endoscope. The arm 101 may manipulate the surgical tool that it carries in order to perform aspects of the invasive procedure.

Before an invasive surgical procedure, a member of operating room staff (e.g. a bedside nurse) typically aids in setting up the surgical robotic system 100. During an invasive procedure, the surgical robotic system is typically controlled by a surgeon from a remote console (not shown). It is often also desirable for a member of operating room staff to be present adjacent to the operating table 103 during the invasive medical procedure—such that they can tend to the patient (e.g. to clean the surgical site). After an invasive surgical procedure, a member of operating room staff typically aids in decommissioning the surgical robotic system 100.

Thus, improving the safety and ease with which members of the operating room staff can interact with a surgical robotic system—before, during and after an invasive medical procedure—is important.

SUMMARY OF THE INVENTION

According to a first aspect of the invention there is provided a control system of a surgical robot arm, the surgical robot arm comprising a series of joints by which the configuration of that surgical robot arm can be altered and one or more force or torque sensors, each force or torque sensor configured to sense a force or torque at a joint of the series of joints, the control system being configured to control the configuration of the surgical robot arm to be altered in response to an externally applied force or torque by: receiving sensory data from the one or more force or torque sensors indicative of a sensed force or torque at a part of the surgical robot arm resulting from the externally applied force or torque; determining a position of the part of the surgical robot arm using a reference position, whereby the sensed force or torque would be compensated by moving the part of the surgical robot arm to the determined position; sending a command signal to the surgical robot arm to drive the part of the surgical robot arm to the determined position; and updating the reference position if the difference between the reference position and the determined position is greater than a threshold displacement.

The control system may be further configured to iteratively perform a control loop comprising the receiving, determining, sending and updating steps.

The control system may be further configured to maintain, for a subsequent iteration, the reference position used in the determining step of the present iteration if the difference between the reference position and the determined position is less than the threshold displacement.

The reference position may be the position to which the control system is configured to cause the part of the surgical robot arm to be driven when sensory data is received from the one or more force or torque sensors indicative of no external force or torque acting at the part.

Determining the position of the part of the surgical robot arm using the reference position may comprise determining a position that satisfies a mass-spring-damper model having a position term that depends on the reference position and the determined position.

The mass-spring-damper model may take the form, $M\ddot{P}+D\dot{P}+K(P-P_{ref})=-X$, where P is the determined position, $P_{ref}$ is the reference position, X is the sensed force or torque at the part of the surgical robot arm and M, D and K are constants.

The surgical robot arm may further comprise an attachment for a surgical instrument at a distal end of the robot arm, and the control system may be configured to cause the robot arm to operate in: a surgical mode in which a surgical instrument attached to the attachment is inside a patient's body; and an instrument retract mode in which the surgical instrument is retracted from the patient's body in response to the externally applied force or torque.

The part of the robot arm may be a point defined with respect to the distal end of the robot arm or a point defined with respect to the surgical instrument.

The sensory data may be received from two or more force or torque sensors and may be indicative of sensed forces or torques at two or more joints of the series of joints resulting from the externally applied force or torque, and the control system may be further configured to: resolve said sensory data so as to determine the force or torque at the defined point resulting from the externally applied force or torque.

The control system may be further configured to, in the instrument retract mode: resolve the sensory data so as to determine the components of the sensed force or torque parallel with the longitudinal axis of the surgical instrument attached to the attachment; and determine the position of the defined point of the surgical robot arm using the reference position, whereby only the resolved components of the sensed force or torque would be compensated by moving the point of the surgical robot arm to the determined position, such that the determined position is constrained to be on the axis parallel with the longitudinal axis of the surgical instrument.

The threshold displacement may be a linear displacement along the axis parallel with the longitudinal axis of the surgical instrument.

The control system may be further configured to control the configuration of the surgical robot arm to be altered in response to an externally applied force or torque by: receiving sensory data from a force or torque sensor indicative of a sensed force or torque at a revolute joint of the series of joints resulting from the externally applied force or torque, the rotational axis of the revolute joint being parallel with the longitudinal axis of the surgical instrument; determining an angular position of the revolute joint using a reference angular position, whereby the sensed force or torque would be compensated by moving the revolute joint to the determined angular position; sending a command signal to the surgical robot arm to drive the revolute joint to the determined angular position; and updating the reference angular position if the difference between the reference angular position and the determined angular position is greater than a threshold displacement.

The control system may be further configured to iteratively perform a control loop comprising the receiving, determining, sending and updating steps.

The control system may be further configured to maintain, for a subsequent iteration, the reference angular position used in the determining step of the present iteration if the difference between the reference angular position and the determined angular position is less than the threshold displacement.

The reference angular position may be the angular position to which the control system is configured to cause the revolute joint to be driven when no external force is sensed at the revolute joint.

Determining the angular position of the revolute joint using the reference angular position may comprise determining an angular position that satisfies a mass-spring-damper model having a position term that depends on the reference angular position and the determined angular position.

The mass-spring-damper model may take the form, $M\ddot{\theta}+D\dot{\theta}+K(\theta-\theta_{ref})=-X$, where $\theta$ is the determined angular position, $\theta_{ret}$ is the reference angular position, X is the sensed force or torque at the revolute joint of the surgical robot arm and M, D and K are constants.

The part of the surgical robot arm may be a joint of the series of joints and the maximum displacement may be an angular displacement of the joint.

The surgical robot arm may further comprise one or more motors, each motor being configured to drive a joint of the series of joints in response to the command signal sent by the control system.

According to a second aspect of the present invention there is provided a method of controlling a surgical robot arm, the surgical robot arm comprising a series of joints by which the configuration of that surgical robot arm can be altered and one or more force or torque sensors, each force or torque sensor configured to sense a force or torque at a joint of the series of joints, the method comprising controlling the configuration of the surgical robot arm to be altered in response to an externally applied force or torque by: receiving sensory data from the one or more force or torque sensors indicative of a sensed force or torque at a part of the surgical robot arm resulting from the externally applied force or torque; determining a position of the part of the surgical robot arm using a reference position, whereby the sensed force or torque would be compensated by moving the part of the surgical robot arm to the determined position; sending a command signal to the surgical robot arm to drive the part of the surgical robot arm to the determined position; and updating the reference position if the difference between the reference position and the determined position is greater than a threshold displacement.

BRIEF DESCRIPTION OF THE DRAWINGS

The present invention will now be described by way of example with reference to the accompanying drawings. In the drawings.

DETAILED DESCRIPTION OF THE DRAWINGS

The following description is presented to enable any person skilled in the art to make and use the invention, and is provided in the context of a particular application.

Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Figure 1:
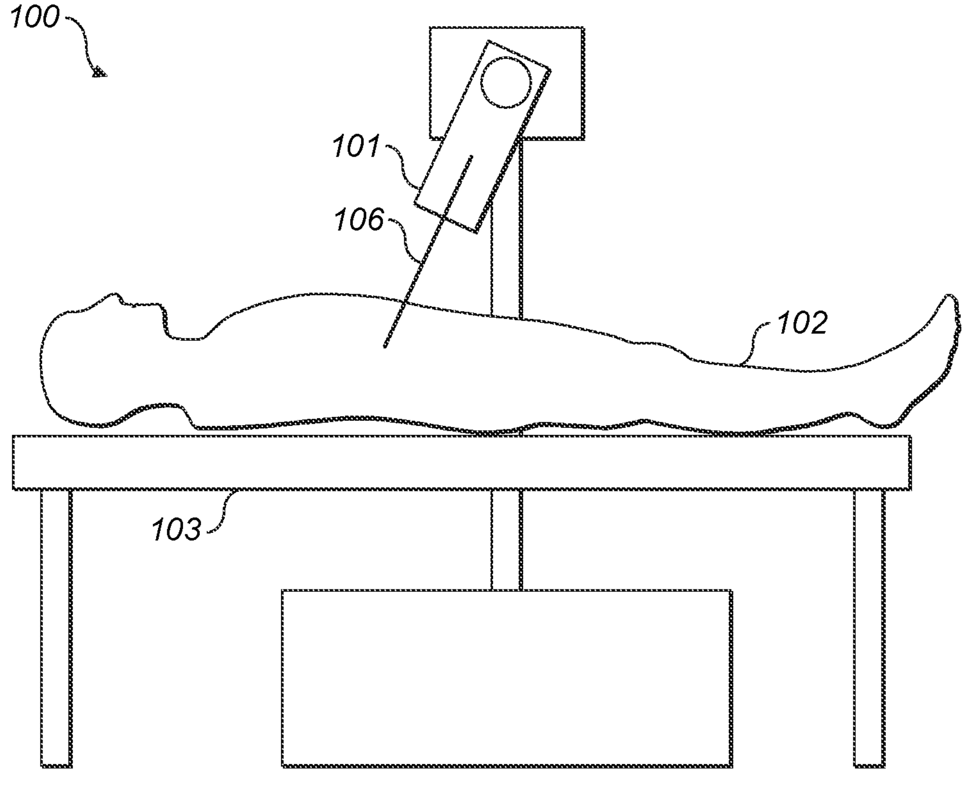
FIG. 1 shows a typical surgical robotic system.
Figure 2:
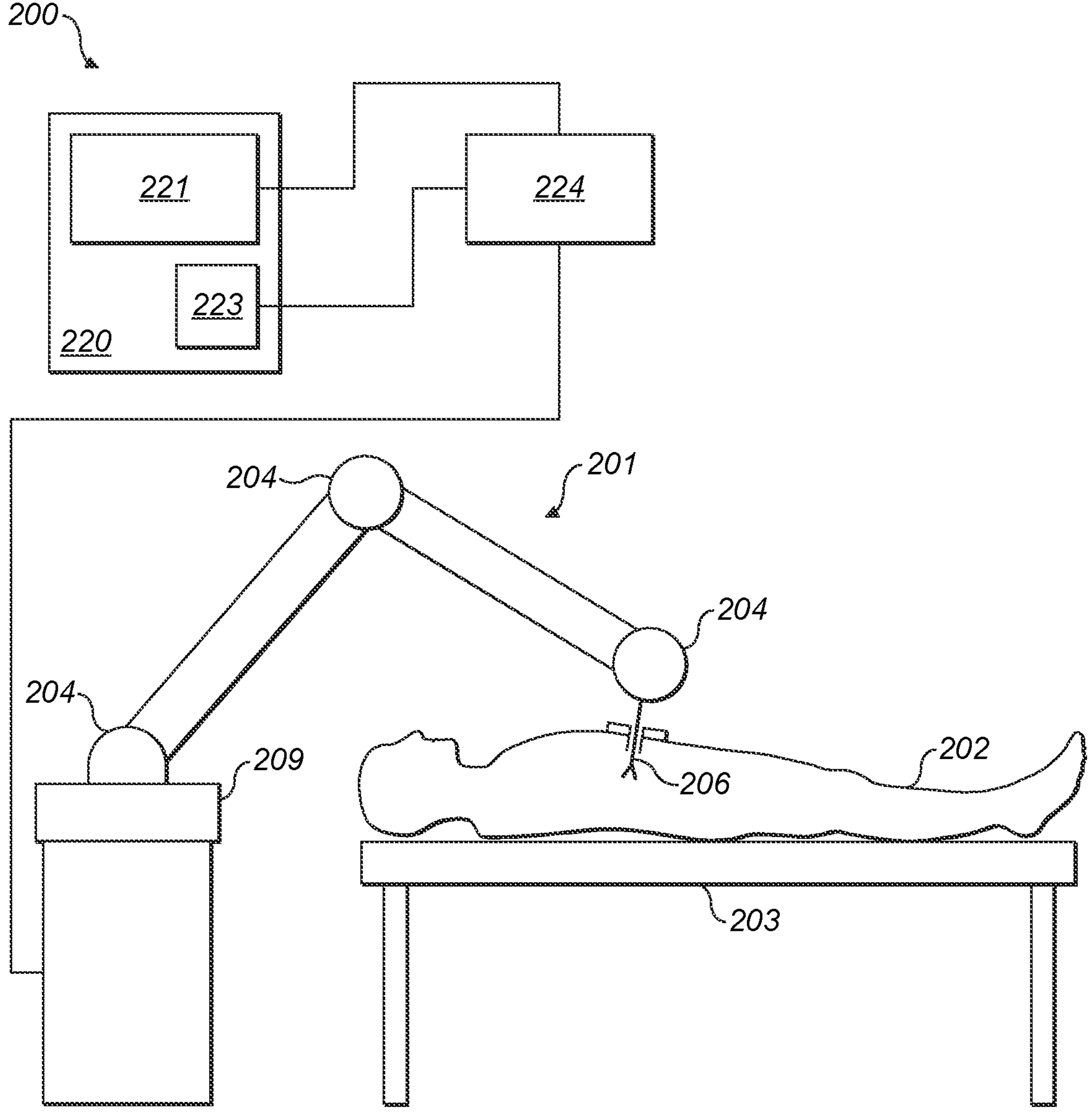
FIG. 2 shows a surgical robotic system.

FIG. 2 shows a surgical robotic system. FIG. 2 shows a surgical robotic system 200 performing an invasive medical procedure on a patient 202. The patient 202 is positioned on an operating table 203. The surgical robotic system 100 comprises a robot arm 201. Although one robot arm 201 is shown in FIG. 2, it is to be understood that a surgical robotic system may comprise any number of robot arms. The robot arm 201 extends from a base 209 at its proximal end. The robot arm 201 comprises a plurality of joints 204 by which the configuration of the robot arm can be altered.

The robot arm 201 comprises an attachment for a surgical instrument 206 at its distal end. The surgical instrument may have a thin elongate shaft with an end effector at its distal end for performing aspects of the invasive procedure. The thin elongate shaft of the surgical instrument may define its longitudinal axis. The surgical instrument could, for example, be a cutting or grasping device, or an imaging device (such as an endoscope). The surgical instrument 206 is insertable into a patient's body 202. The surgical instrument 206 may be inserted into a patient's body 202 via a port.

The configuration of the robot arm 201 may be remotely controlled in response to inputs received at a remote surgeon console 220. A surgeon may provide inputs to the remote console 220. The remote surgeon console comprises one or more surgeon input devices 223. For example, these may take the form of a hand controller and/or foot pedal. The surgeon console also comprises a display 221.

A control system 224 connects the surgeon console 220 to the surgical robot arm 201. The control system receives inputs from the surgeon input device(s) and converts these to control signals to move the joints of the robot arm 201 and surgical instrument 206. The control system 224 sends these control signals to the robot arm, where the corresponding joints are driven accordingly. The control system 224 may be separate from the remote surgeon console 220 and the robot arm 201. The control system 224 may be collocated with the remote surgeon console 220. The control system

224 may be collocated with the robot arm 201. The control system 224 may be distributed between the remote surgeon console 220 and the robot arm 201.

The configuration of the robot arm 201 may be controllable in response to external forces applied directly to that robot arm. For example, a member of the bedside team (e.g. an operating room nurse) may apply forces or torques directly to a robot arm (e.g. by pushing a joint of the robot arm). This behaviour will be described in further detail herein.

Figure 3:
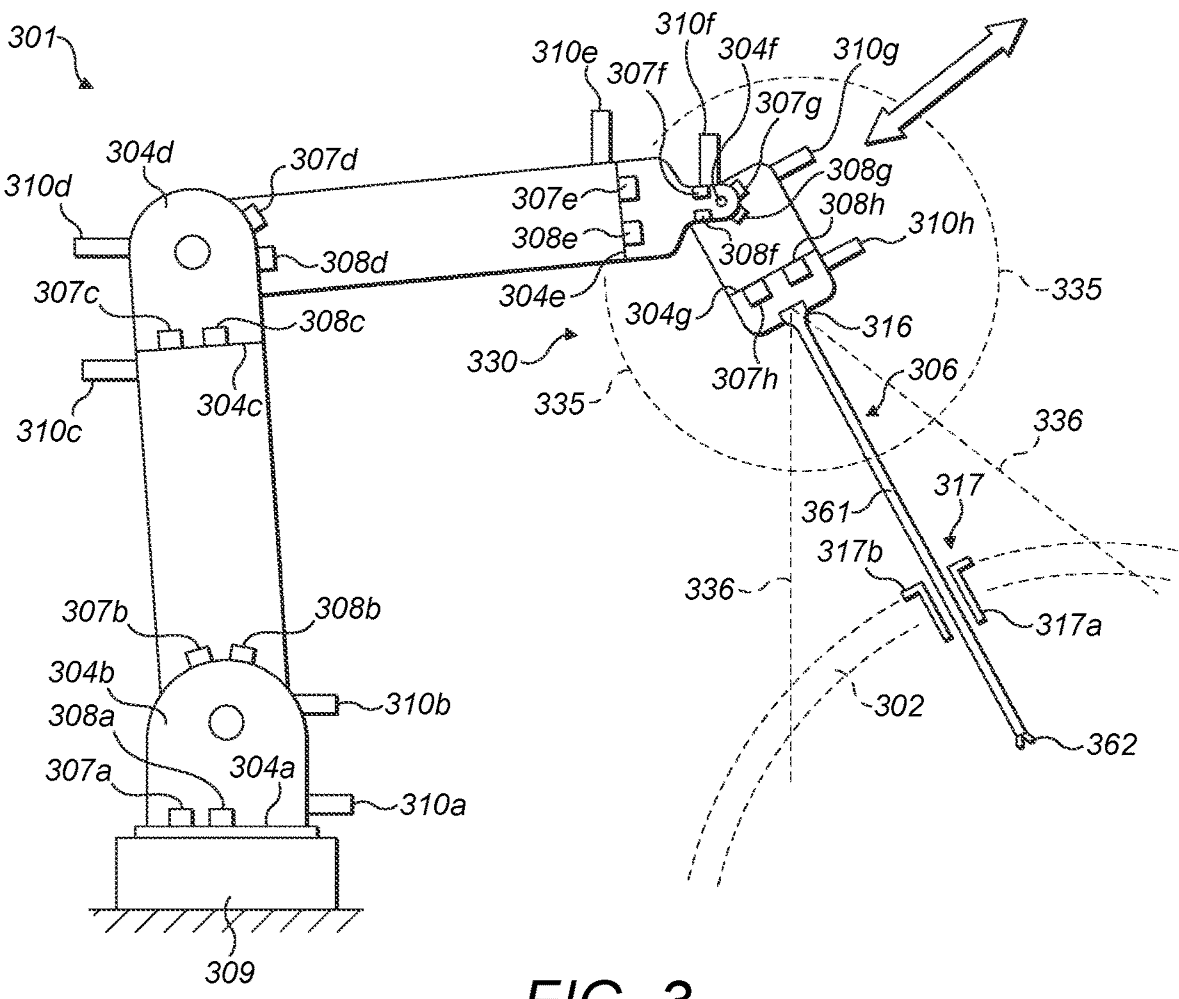
FIG. 3 shows a surgical robot arm of a surgical robotic system.

FIG. 3 shows an example of a robot arm 301. The robot arm 201 shown in FIG. 2 may have the same features as the robot arm 301 shown in FIG. 3.

The robot arm comprises a base 309. The robot arm has a series of rigid arm members. Each arm member in the series is joined to the preceding arm member by a respective joint 304*a-g*. Joints 304*a-e* and 304*g* are revolute joints. Joint 304*f* is composed of two revolute joints whose axes are orthogonal to each other, as in a Hooke's or universal joint. The point at which the axes of joints 304*e-g* intersect may be termed the "wrist". A robot arm could be jointed differently from the arm of FIG. 3. For example, joint 304*d* could be omitted and/or joint 304*f* could permit rotation about a single axis. The robot arm could include one or more joints that permit motion other than rotation between respective sides of the joint, such as a prismatic joint by which an instrument attachment can slide linearly with respect to more proximal parts of the robot arm.

The joints are configured such that the configuration of the robot arm can be altered allowing the distal end 330 of the robot arm to be moved to an arbitrary point in a three-dimensional working volume illustrated generally at 335. One way to achieve that is for the joints to have the arrangement illustrated in FIG. 3. Other combinations and configurations of joints could achieve a similar range of motion, at least within the zone 335. There could be more or fewer arm members.

The distal end of the robot arm 330 has an attachment 316 by means of which a surgical instrument 306 can be releasably attached. The surgical instrument has a linear rigid shaft 361 and an end effector 362 at the distal end of the shaft. The end effector 362 consists of a device for engaging in a procedure, for example a cutting, grasping or imaging device. As described herein, terminal joint 304*g* may be a revolute joint. The surgical instrument 306 and/or the attachment 316 may be configured so that the instrument extends linearly parallel with the rotation axis of the terminal joint 304*g* of the robot arm. In this example the instrument extends along an axis coincident with the rotation axis of joint 304*g*.

Joints 304*e* and 304*f* of the robot arm are configured so that with the distal end of the robot arm 330 held at an arbitrary location in the working volume 335 the surgical instrument 306 can be directed in an arbitrary direction within a cone. Such a cone is illustrated generally at 336. One way to achieve that is for the terminal part of the arm to comprise the pair of joints 304*e* and 304*f* whose axes are mutually arranged as described above. In fact, in examples where joint 304*e* is a revolute joint and joint 304*f* is a composed of two revolute joints (as described herein), this joint arrangement can permit the surgical instrument to be directed in an arbitrary direction on a spherical surface (not shown). Other mechanisms can achieve a similar result. For example, joint 304*g* could influence the attitude of the instrument if the instrument extends in a direction which is not parallel to the axis of joint 304*g*.

The surgical instrument 306 may be inserted into the patient's body through a port 317. The port 317 may comprise a hollow tube 317*a*. The hollow tube 317*a* may pass through the outer tissues 302 of the patient so as to limit disruption to those tissues as the surgical instrument is inserted and removed, and as the instrument is manipulated within the patient's body. The port 317 may comprise a collar 317*b*. The collar 317*b* may prevent the port 317 being inserted too far through the outer tissues 302 of the patient.

The robot arm 301 comprises a series of motors 310*a-h*. With the exception of the compound joint 304*f*, which is served by two motors, each motor is arranged to drive rotation about a respective joint of the robot arm. The motors are controlled by a control system (such as control system 224 shown in FIG. 2). The control system may comprise a central controller, one or more arm controllers and one or more joint controllers. The central controller may exert control over the robotic surgical system (e.g. including one or more robot arms). Each robot arm controller may exert control over a robot arm. Each joint controller may exert control over one or more joints of the series of joints of a robot arm. Each of the central controller, arm controller and joint controller may comprise a processor and a memory. The memory stores, in a non-transient way, software code that can be executed by the processor to cause the processor to output a control signal in the manner described herein. In other examples, the control system may comprise a single controller, a pair of controllers, or any other number of controllers, configured to perform the functions of the central controller, one or more arm controllers and one or more joint controllers described herein.

The robot arm 301 may comprise a series of sensors 307*a-h* and 308*a-h*. These sensors may comprise, for each joint, one or more position sensors 307*a-h* for sensing the rotational position of the joint and a force or torque sensor 308*a-h* for sensing a force or torque applied about the joint's rotation axis. Compound joint 304*f* may have two sets of sensors. The position and/or force or torque sensors for a joint may be integrated with the motor for that joint. In an example, each joint may comprise two position sensors, including a first position sensor at the motor and a second position sensor directly at the joint. The robot arm may also comprise one or more current sensors to measure the current provided at one or more of the motors 310*a-h* in order to ensure that the current actually supplied to a motor corresponds with the current demanded by the control system for that motor. The outputs of the sensors are passed to the control system where they form inputs for the processor.

The control system receives sensory data from the position sensors 307*a-h* and force or torque sensors 308*a-h*. From the position sensors the control system can determine the current configuration of the robot arm. For example, the control system may store for each element of the robot arm (e.g. the joints and the arm members), and the surgical instrument, its mass, the distance of its centre of mass from the preceding joint of the robot arm and the relationship between the centre of mass and the positional output of the position sensor for the preceding joint. The current configuration of the robot arm could be inferred by other means. Using that information, the control system can model the effect of gravity on the components of the robot arm for the current configuration of the robot arm and estimate a force or torque due to gravity on each joint of the robot arm. The control system can then drive the motor 310*a-h* of each joint to apply a force or torque that will exactly oppose the calculated gravitational force such that the configuration of the robot arm is maintained despite the action of gravity.

Members of the operating room staff (e.g. an operating room nurse) can interact with the surgical robotic arm 301—before, during and after an invasive medical procedure. In order to improve the ease and safety with which such interactions take place, the control system (e.g. control system 224 in FIG. 2) can control the configuration of the robot arm 301 in response to forces applied directly to a robot arm by members of the operating room staff (e.g. by pushing a joint of the robot arm). The control system 224 is configured to receive sensory data from the force or torque sensors 308*a*-*h* indicative of a sensed force or torque at the surgical robot arm resulting from the externally applied force or torque, process the received sensory data, and send a command signal to the surgical robot arm to drive the robot arm such that the configuration of the robot arm is altered so as to comply with the externally applied force or torque.

The control system may cause the surgical robot arm 301 to be operated in a number of different modes—in which the commanded response of the robot arm to an externally applied force or torque is different. In order to achieve this, the processing performed by the control system on the received sensory data may be different in each of these modes. Three examples of such modes are a compliant mode, a surgical mode, and an instrument retract mode. These modes will be described in further detail herein.

Compliant Mode

In the compliant mode, the control system commands the surgical robot arm such that its configuration can be altered in response to an externally applied force or torque. In this way, an operating room nurse can push or pull any part of the robot arm to a desired position, and the part will move to that desired position and stay in that position notwithstanding the effect of gravity on it and on any parts depending from it. The behaviour of the robot arm in this mode may be termed compliant behaviour. The compliant mode can be used by members of the operating room staff before or after an invasive medical procedure (e.g. during operating room set up or clean up). As described further herein, the control system may also cause certain parts of the robot arm to exhibit compliant-like behaviour during an invasive medical procedure.

For example, the compliant mode can be used to insert the surgical instrument into port 317 in the patient's body. That is, the compliant mode may be used to insert an end effector 362 of the surgical instrument into the port 317. With reference to FIG. 3, an operator (e.g. member of the operating room team) can grasp one or both of the robot arm 301 and the surgical instrument 306. The operator can then apply external forces or torques which the control system responds to by altering the configuration of the robot arm 301 such that the elongate axis of the shaft 361 of the instrument is roughly aligned with the passageway through the hollow tube 317*a* of the port 317. The operator can then apply an external force (e.g. a push or pull) or torque (e.g. a twist) to the robot arm and/or the instrument which the control system responds to by moving the instrument roughly parallel to its elongate axis and into the passageway in the port 317.

Figure 4:
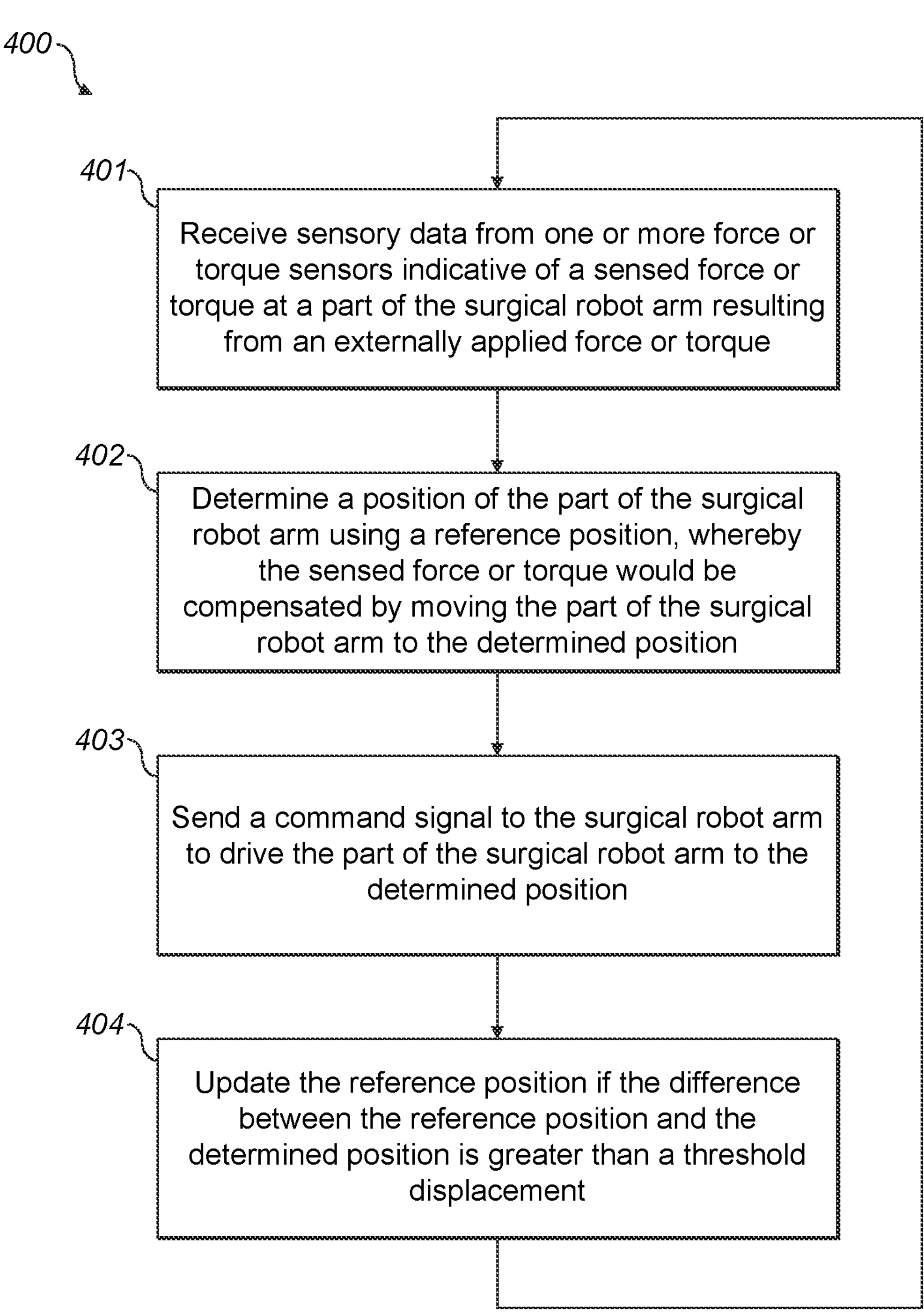
FIG. 4 is a flow diagram showing a first control loop performed by a control system to alter the configuration of a surgical robot arm in response to an externally applied force or torque.

FIG. 4 is a flow diagram showing a first set of steps performed by a control system to alter the configuration of a surgical robot arm in response to an externally applied force or torque. The control system may be configured to perform multiple iterations of the set of steps shown in FIG. 4. That is, the control system may perform steps 401, 402, 403 and 404 in sequence, followed by returning to step 401 to repeat that sequence. In other words, FIG. 4 is a flow diagram showing a first control loop performed by a control system to alter the configuration of a surgical robot arm in response to an externally applied force or torque.

In step 401, sensory data is received from the one or more force or torque sensors on the robot arm indicative of a sensed force or torque at a part of the surgical robot arm resulting from the externally applied force or torque. The received sensory data may in fact be indicative of a force or torque resulting from the effect of gravity on the part of the robot arm as well as a force or torque resulting from the externally applied force or torque at the part of the surgical robot arm. The received sensory data may also be indicative of vibrations, inertia and/or accelerations at the part of the robot arm as well as a force or torque resulting from the externally applied force or torque at the part of the surgical robot arm. The control system may be able to distinguish between gravitational forces, external forces and vibrations, inertia and/or accelerations at the part of the robot arm by filtering the sensory data. For example, a low pass filter may be used to identify vibrations at the part of the robot arm, because torque measurements relating to arm vibrations are typically higher in frequency than those resulting from gravitational forces and externally applied forces or torques. As described herein, the control system can model the effect of gravity on the components of the robot arm for the current configuration of the robot arm and thereby estimate a force or torque due to gravity on a part of the of the robot arm. Thus, the sensory data may first be adjusted so as to discount the force or torque caused by the effect of gravity on the part of the robot arm, and/or any vibrations, inertia and/or accelerations at that part of the robot arm. For example, the force or torque caused the effect of gravity on the part of the robot arm and/or vibrations, inertia and/or accelerations at the part of the robot arm may be subtracted from the sensory data. Alternatively, the sensory data may be digitally analysed (e.g. by filtering the sensory data as described in this paragraph), with the control system only taking account of only the force or torque resulting from the externally applied force or torque.

The control system may consider the force or torque acting at each joint of the series of joints of the robot arm independently. In this case, the part of the robot arm is a joint of the series of joints.

Instead, the part of the robot arm may be a point defined with respect to the robot arm or a point defined with respect to the surgical instrument. A point defined with respect to the robot arm may be on the robot arm, or may not be on the robot arm but have a fixed spatial relationship with respect to the robot arm. A point defined with respect to the surgical instrument may be on the surgical instrument, or may not be on the surgical instrument but have a fixed spatial relationship with respect to the surgical instrument. For example, the point may be the "wrist".

An externally applied force or torque at a defined point of the robot arm or the instrument may result in a force or torque at multiple joints of the robot arm. Thus, the sensory data may include sensed force of torque data from a plurality of force or torque sensors, which are resolved by the control system so as to determine the force or torque resulting from the externally applied force or torque at the defined point. In order to determine a resulting force or torque at a defined point from measured forces or torques acting locally at each of a plurality of joints, the direction of the axis of rotation for each joint in the global frame of reference may be considered. In this way, forward kinematics may be used to determine the contribution of a force or torque measured at each joint to the force or torque acting at a defined point. It is also possible for the control system to concurrently consider the force or torque acting at a defined point and at a certain joint of the series of joints. That is, the control system may consider in parallel: (i) the force or torque acting at a defined point and (ii) the force or torque acting at a certain joint of the series of joints of the robot arm.

In step 402, a position of the part of the surgical robot arm is determined using a reference position, whereby the sensed force or torque would be compensated by moving the part of the surgical robot arm to the determined position. That is, the position is determined such that the sensed force or torque resulting from the externally applied force or torque would be complied with, conformed with or reduced (e.g. to zero) by moving the part of the surgical robot arm to that determined position. The reference position is the position to which the control system is configured to cause the part of the surgical robot arm to be driven when no external force or torque is acting at the part. For example, the reference position may be the position of the part of the robot arm before the external force was applied. The reference position may initially be determined using the position sensors 307*a-h*. Alternatively, the reference position may initially be user-determined, for example, by an input received at the surgeon input device. Thereafter, the reference position may be iteratively updated as is described further herein.

Determining the position of the part of the surgical robot arm using the reference position may comprise determining a position that satisfies a mass-spring-damper model having a position term that depends on the reference position and the determined position. Examples 1 and 2 are detailed examples illustrating how step 402 may be performed.

Example 1

In Example 1, the part of the robot arm is a joint, j, of the series of joints of the robot arm and the sensory data is indicative of a sensed torque, $\tau_j$, at that joint resulting from the externally applied force or torque. An angular position, $\theta_j$, of the joint is determined using a reference position, $\theta_{j,\,ref}$. The angular position, $\theta_j$, is determined as the position $\theta_j$ that satisfies:

$$M\ddot{\theta}_j+D\dot{\theta}+K(\theta_j-\theta_{j,ref})= \qquad \text{(Equation 1)}$$

where M, D and K are constants. For example, M may be a mass constant, D may be a damping constant, and K may be a spring constant. $K(\theta_j-\theta_{j,ref})$ is a position term dependent on the determined position and the reference position. $D\dot{\theta}_j$ is a velocity term dependent on a first derivative with respect to time of the determined position. $M\ddot{\theta}_j$ is an acceleration term dependent on a second derivative with respect to time of the determined position. The velocity, $\dot{\theta}_j$ may be approximated by dividing the difference between successive angular positions of the joint, j, by the sampling rate. Similar approximations may be made for the acceleration, $\ddot{\theta}_j$.

An angular position, $\theta_j$, for each joint of the series of joints may be independently determined in accordance with Example 1.

Example 2

In Example 2, the part of the robot arm is a defined point, p, and the sensory data is indicative of a sensed force, $f_p$, acting in a direction at the defined point resulting from the externally applied force or torque. The direction is a direction with respect to which the sensed force is defined. The direction need not correspond to a geometric feature of the robot arm. A position, $S_p$, of the point is determined using a reference position, $S_{p,\,ref}$. The position, $S_p$, is determined as the position, $S_p$, that satisfies:

$$M\ddot{S}_p+DS_pK(S_p-S_{p,ref})-f_P \qquad \text{(Equation 2)}$$

where M, D and K are constants. For example, M may be a mass constant, D may be a damping constant, and K may be a spring constant. $K(S_p-S_{p,\,ref})$ is a position term dependent on the determined position and the reference position. $DS_p$ is a velocity term dependent on a first derivative with respect to time of the determined position. $M\ddot{S}_p$ is an acceleration term dependent on a second derivative with respect to time of the determined position. The velocity, $\dot{\theta}_j$, may be approximated by dividing the difference between successive angular positions of the joint, j, by the sampling rate. Similar approximations may be made for the acceleration, $\ddot{\theta}_j$.

Returning to FIG. 4, in step 403, a command signal is sent to the surgical robot arm to drive the part of the surgical robot arm to the determined position. The control system may use inverse kinematics to determine the angular positions of the joints of the series of joints of the robot arm required for the part of the surgical robot to be positioned in the determined position. The control system may control one or more of motors 310*a-h* so as to drive the part of the surgical robot arm to the determined position. In this way, the member of the bedside staff may feel that that the robot arm is moving freely in response to the force or torque they are applying—when in fact it is the motors of the robot arm driving the movement.

Returning to Examples 1 and 2, the M, D and K constants may affect the "feel" of the robot arm to the member of operating room staff who is interacting with the robot arm. The mass constant, M, is an inertial term and can determine how readily the control system causes the part of the robot arm to accelerate/decelerate in response to a force or torque. The damping constant, D, can determine how readily the control system causes the part of the robot arm to react to varying forces or torques. For example, the damping constant, D, may be set such that the control system does not readily cause the robot arm to move in response to high frequency forces or torques, such as vibrations—in contrast to lower frequency forces or torques, such as pushes or twists applied by a member of the bedside team. For example, vibrations can be caused by motor vibrations that may arise due to friction. It would be undesirable for the control system to cause the configuration of the robot arm to be changed in response to the high frequency forces or torques caused by those vibrations. Thus, the M and D constants may be chosen so that mass-spring-damper model acts as a digital filter—filtering out such high-frequency forces or torques. The spring constant, K, can determine the amount of force or torque required for the control system to cause a change in position of the part of the robot arm. The M, D and K constants may be predetermined and stored as an input by the control system. The M, D and K constants may be user configurable, e.g. so that a member of the operating room staff can change the "feel" of the robot arm in accordance with their personal preferences. Different M, D and K constants may be set for use in different modes.

In step 404, the reference position is updated if the difference between the reference position and the determined position is greater than a threshold displacement. If the difference between the reference position and the determined position is less than the threshold displacement, then the control system maintains, for the next or subsequent iteration, the reference position used in step 402 of the present iteration of the control loop. As described herein, the reference position is the position to which the control system is configured to cause the part of the surgical robot arm to be driven when no external force is acting at the part. Thus, in this way, the control system can cause the robot arm to behave "elastically" or "plastically" in response to an externally applied force or torque. Elastic behaviour means that the robot arm is displaced from a position in response to an externally applied force or torque, but returns to that position when the externally applied force or torque is no longer being applied. Elastic behaviour occurs when the reference position is not updated in successive iterations of the control loop. Plastic behaviour means that the robot arm is displaced from a position in response to an externally applied force or torque, and retains that position even when the externally applied force or torque is no longer being applied. Plastic behaviour occurs when the reference position is updated in successive iterations of the control loop.

The threshold displacement may be predetermined and stored as an input by the control system. The magnitude of the threshold displacement may affect the "feel" of the robot arm to the member of operating room staff who is interacting with the robot arm. That is, the magnitude of the threshold displacement may be a determining factor in whether the control system causes the robot arm to behave "elastically" or "plastically" in response to an amount of externally applied torque or force. A different threshold displacement may be set for use in different modes. The threshold displacement may be user configurable, e.g. so that a member of the operating room staff can change the "feel" of the robot arm in accordance with their personal preferences.

In an example, referring back to Example 1, the threshold displacement may be represented by $\theta_{displacement}$ The reference position $\theta_{j,\ ref}$ may be updated if the following condition is met: $\|\theta_{j,\ ref}-\theta_j\|>\theta_{displacement}$ The reference position $\theta_{j,\ ref}$ may be updated to be equal to $\theta_j\pm\theta_{displacement}$ In this way, the robot arm may behave plastically when the sensed torque exceeds $K\times\theta_{displacement}$ for a threshold period of time. $K\times\theta_{displacement}$ is a torque constant, as both K and $\theta_{displacement}$ are constants. Thus, the robot arm may behave plastically when the sensed torque exceeds a torque constant for a threshold period of time. The threshold period of time depends on how quickly the robot arm reaches the determined position (e.g. the velocity and acceleration with which the control system commands the robot arm to move—which may dependent on the velocity and acceleration terms of the mass-spring-damper model described herein respectively) and how frequently the control system determines whether to update the reference position. For example, the control system may assess whether the reference position should be updated at a frequency of 5 kHz. The frequency may be predetermined and stored as an input by the control system. The frequency may affect the "feel" of the robot arm to the member of operating room staff who is interacting with the robot arm. A different frequency may be set for use in different modes.

Figure 5:
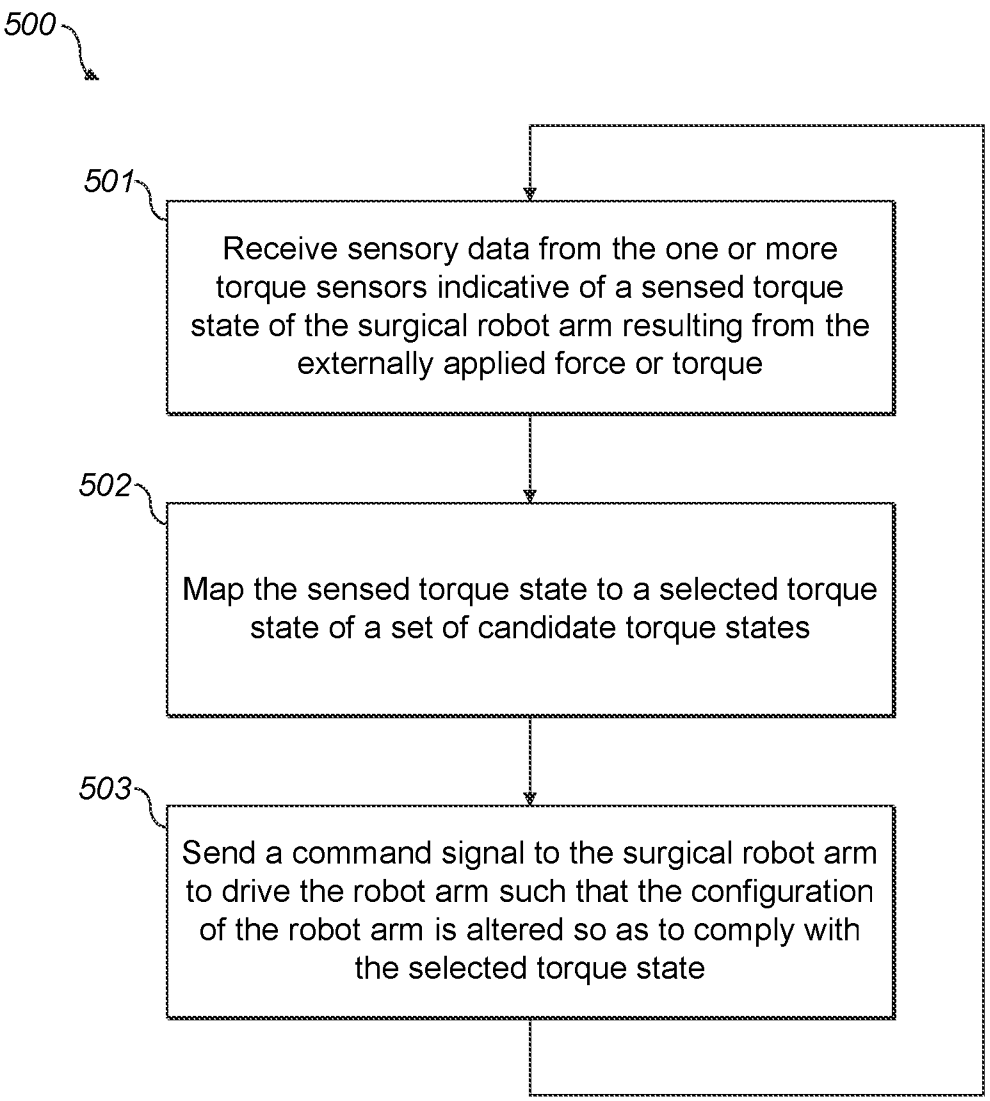
FIG. 5 is a flow diagram showing a second control loop performed by a control system to alter the configuration of a surgical robot arm in response to an externally applied force or torque.

FIG. 5 is a flow diagram showing a second set of steps performed by a control system to alter the configuration of a surgical robot arm in response to an externally applied force or torque. The set of steps described with reference to FIG. 5 may be used in combination with the set of steps described with reference to FIG. 4. The set of steps described with reference to FIG. 5 may also be used independently of the set of steps described with reference to FIG. 4.

The control system may be configured to perform multiple iterations of the set of steps shown in FIG. 5. That is, the control system may perform steps 501, 502 and 503 in sequence, followed by returning to step 501 to repeat that sequence. In other words, FIG. 5 is a flow diagram showing a second control loop performed by a control system to alter the configuration of a surgical robot arm in response to an externally applied force or torque.

The set of steps described with reference to FIG. 5 may be used when the robot arm comprises one or more torque sensors 308*a-h*, each torque sensor being configured to sense a torque at a joint of the series of joints of the robot arm. The sensory data provided by certain torque sensors can contain interference, such as noise. That is, the sensory data can include a number of anomalous values, outlying values, and/or erroneous values due to factors external to those of interest. Thus, whilst it is possible to use the raw sensory data output by the torque sensors (e.g. in step 402 of FIG. 4), it is preferable to further process the sensory data in order to reduce the amount of noise it contains.

In step 501, the control system receives sensory data from the one or more torque sensors indicative of a sensed torque states of the surgical robot arm resulting from the externally applied force or torque. As described herein, the received sensory data may in fact be indicative of a torque resulting from the effect of gravity on the part of the robot arm, and/or any vibrations, inertia and/or accelerations at that part of the robot arm, as well as a torque resulting from the externally applied force or torque at the part of the surgical robot arm. Thus, the sensory data may first be adjusted for the torque caused the effect of gravity on the part of the robot arm, and/or any vibrations, inertia and/or accelerations at that part of the robot arm.

In step 502, the sensed torque state is mapped to a selected torque state of a set of candidate torque states. The set of candidate torque states may be a set of permissible torque states for the robot arm. The set of candidate torque states may be encoded in a function. The set of candidate torque states may be predetermined.

Figure 6:
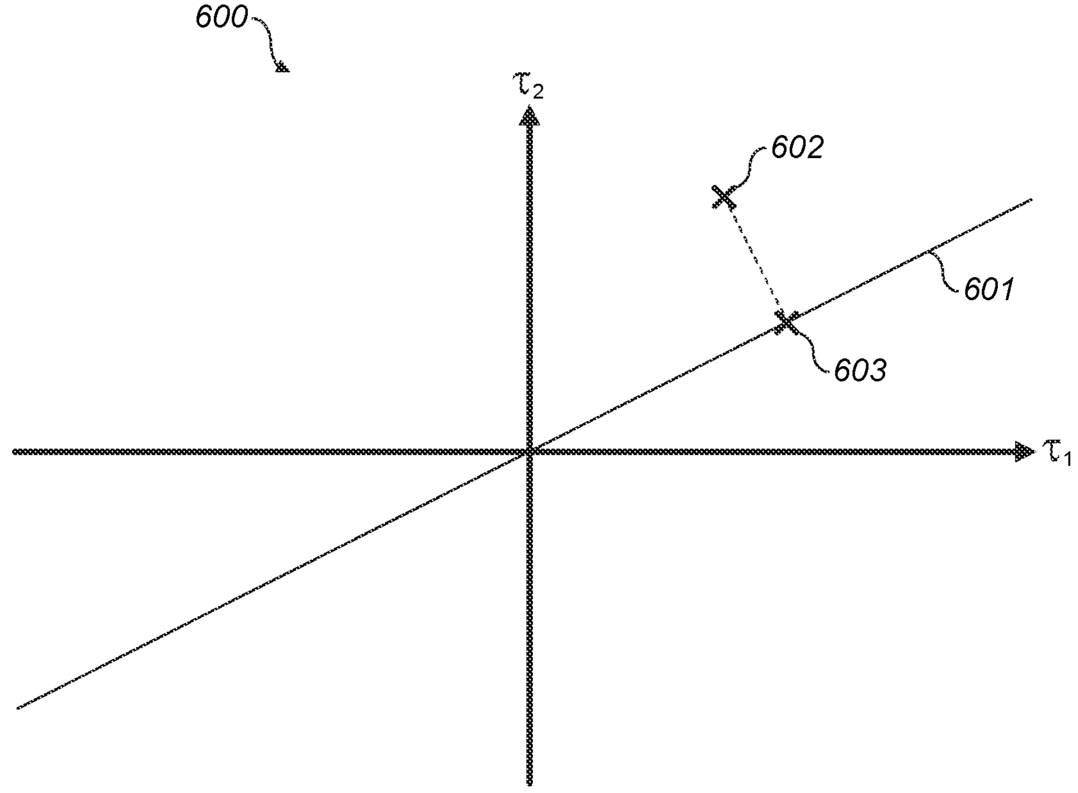
FIG. 6 is a schematic diagram showing the mapping of a sensed torque state to a selected torque state of a set of candidate torque states in two-dimensions.

FIG. 6 is a schematic diagram 600 showing the mapping of a sensed torque state 602 to a selected torque state 601 of a set of candidate torque states 601 in two-dimensions. In FIG. 6, the set of candidate torque states is encoded in a linear function 601. The sensed torque state 602 is not a solution of the linear function 601—e.g. it lies outside of the set of states to which the function maps. The sensed torque state 602 is mapped, or projected, to the closest torque state that is a solution to that linear function 601—in this case, selected torque state 603. The selected torque state 603 may be the torque state of the set of candidate torque states having the lowest Euclidian distance or least squares distance to the sensed torque state 602. The selected torque state 603 may be determined by iteratively refining an approximation of which torque state of the set of candidate torque states has the lowest Euclidian distance or least squares distance to the sensed torque state 602.

The sensed torque state may be represented by a column vector comprising torque data received from each of the one or more torque sensors. The torque state may be represented in any other appropriate manner. Each torque state in the set of candidate torque states may correspond with a respective one or more forces. Each torque state may be a product of its respective one or more forces and a Jacobian matrix. Torque states may be expressed in joint space. Forces may be expressed in cartesian coordinates. The Jacobian matrix may transform the changes in joint space to the changes in cartesian coordinates. Each torque state in the set of candidate torque states may be an element of the image of the Jacobian matrix. The image of a matrix is the set of values to which that matrix can map.

Example 3 is a detailed example illustrating how step 502 may be performed.

Example 3

In Example 3, a single point, p, is defined with respect to the robot arm or with respect to the instrument. For an external force, f, applied at p it is possible to deduce the force f by applying the principle of virtual work to the net joint torques, τ. The net joint torques, r, may be termed the torque state, and can be represented by a column vector comprising torque data received from each of the one or more torque sensors. According to this principle, if moving the point, p, a distance, $\delta\hat{f}$, requires joint, j, of the series of joints to move by an angle $\vartheta_9$, then if a force is applied at p in the direction of $\hat{f}$ the torque $\tau_j$ seen by joint j is proportional to $$\frac{\delta}{\vartheta_j}.$$

This can be expressed by:

$$\tau_j = \|f\|\frac{\delta}{\vartheta_j}.$$

This information can be encoded in the Jacobian, $J_p$ in accordance with:

$$\tau = \begin{pmatrix} \tau_1 \\ \vdots \\ \tau_n \end{pmatrix} = \begin{pmatrix} \frac{\partial p_x}{\partial \theta_1} & \cdots & \frac{\partial p_z}{\partial \theta_1} \\ \vdots & \ddots & \vdots \\ \frac{\partial p_x}{\partial \theta_n} & \cdots & \frac{\partial p_z}{\partial \theta_n} \end{pmatrix} f = J_p f \quad \text{(Equation 3)}$$

The Jacobian $J_p$ represents how much a small change in the net joint angles $\theta=(\theta_1, \ldots, \theta_n)$ will move the point p. Each of the joints in the series of joints of the robot arm may be considered. That is, the column vector may comprise torque data received from torque sensors at each of the joints 304*a*-*g*. Alternatively, a subset of the joints in the series of joints of the robot arm may be considered. For example, only the joints adjacent to the defined point, p, may be considered—or any number of joints either side of the defined point.

As described herein, the sensory data indicative of the sensed torque state, τ, often contains noise interference. Thus, there are a number of sensed torque states for which $\tau \notin \mathrm{Im}(J_p)$. That is, for which the sensed torque state, τ, is not an element of the image of the Jacobian matrix $J_p$. In other words, for one or more sensed torque states, τ, there will not be a force f that is a solution to $f=J_p^{-1}\tau$.

Thus, as described herein, the sensed torque state, τ, is mapped to a selected torque state, $\tilde{\tau}$, of a set of candidate torque states. The selected torque state, $\tilde{\tau}$, is an element of the image of the Jacobian matrix $J_p$. This can be expressed as $\tilde{\tau} \in \mathrm{Im}(J_p)$. The selected torque state, $\tilde{\tau}$, may be the torque state of the set of candidate torque states having the lowest Euclidian distance or least squares distance to the sensed torque state, τ.

Returning to FIG. 5, in step 503, the control system sends a command signal to the surgical robot arm to drive the robot arm such that the configuration of the robot arm is altered so as to comply with, compensate for, or conform with the selected torque state (e.g. $\tilde{\tau}$). For example, the torque data, $\tilde{\tau}_n$, relating to each joint in the selected torque state, $\tilde{\tau}$, may be used as an input to the mass-spring-damper model described with reference to FIG. 4 and Example 1.

Returning to step 502 and Example 3, optionally the control system may determine a force corresponding to the selected torque state. For example, having determined the selected torque state, $\tilde{\tau}$, the control system may determine the corresponding force, f, by solving $f=J_p^{-1}\tilde{\tau}$. The force f may be indicative of a force acting at the defined point as a result of the externally applied force or torque, the force being defined with respect to the direction f defined with respect to the point. Often the Jacobian, $J_p$, will not be invertible. This is because, the number, n, of joints considered often differs from the number cartesian axis (e.g. x, y, z), and so the Jacobian in this case would not be square. Thus, in order to solve $f=J_p^{-1}\tilde{\tau}$, having determined $\tilde{\tau}$, where the Jacobian is not invertible, a right inverse function may be used. Other solutions for approximating the inverse of a matrix that is not invertible also exist.

Alternatively, a Moore-Penrose pseudoinverse of the Jacobian matrix can be used to map the sensed torque state to the selected torque state and determine the force corresponding to the selected torque state in one step. For example, the force, f, could be determined in dependence on the sensed torque state, τ, in accordance with:

$$f=J_p^{+}\tau \quad \text{(Equation 4)}$$

where $J_p^{+}$ is the Moore-Penrose pseudoinverse of $J_p$.

The control system may send a command signal to the surgical robot arm to drive the robot arm such that the configuration of the robot arm is altered so as to comply with, compensate for, or conform with the determined force, f. For example, the force, f, may be used as an input to the mass-spring-damper model described with reference to FIG. 4 and Example 2.

Returning to step 702, rather than determining the force acting at a single point, p, as in Example 3, the control system may alternatively determine at least one force acting at each of n points of the robot arm, where n>1. Example 4 is a detailed example illustrating how step 502 may be performed in this manner.

Example 4

In Example 4, two points are defined with respect to the robot arm. The first point is the "wrist" (e.g. the point at which the axes of joints 304*e*-*g* intersect) and the second point is the "elbow" (e.g. a point defined with respect to joint 304*d*). For an external force, $f_{elbow}$, applied at the elbow it is possible to deduce the force $f_{elbow}$ by applying the principle of virtual work to the net joint torques. The net joint torques may be termed the torque state, and can be represented by a column vector comprising torque data received from each of the one or more torque sensors. According to this principle, if moving the elbow a distance, $\delta\widehat{f_{\text{elbow}}}$, requires joint, j, of the series of joints to move by an angle $\vartheta_j$, then if a force is applied at the elbow in the direction of $\widehat{f_{\text{elbow}}}$ the torque $\tau_j$ seen by joint j is proportional to $$\frac{\delta}{\vartheta_j}.$$

This can be expressed by:

$$\tau_j = \|f_{elbow}\| \frac{\delta}{\vartheta_j}.$$

In Example 4, forces applied at the wrist are considered with respect to three directions, the cartesian directions x, y and z. The x, y and z directions may be defined in a global frame of reference. Alternatively, the x, y and z directions may be defined in a local wrist frame of reference. For example, the z direction may be the same direction as the direction of the instrument, and x and y may be defined perpendicular to that z direction and to each other. In this example, the x, y and z directions may change as the wrist joints are moved. Forces $f_{wrist_x}$, $f_{wrist_y}$ and $f_{wrist_z}$ are addressed in the same manner as described herein for $f_{elbow}$. This information can be encoded in the Jacobian, $J_p$ in accordance with:

$$\begin{pmatrix} f_{elbow} \\ f_{wrist_x} \\ f_{wrist_y} \\ f_{wrist_z} \end{pmatrix} = \begin{pmatrix} \frac{\partial elbow}{\partial \theta_1} & \frac{\partial wrist_x}{\partial \theta_1} & \cdots & \frac{\partial wrist_z}{\partial \theta_1} \\ \vdots & \vdots & \ddots & \vdots \\ \frac{\partial elbow}{\partial \theta_n} & \frac{\partial wrist_x}{\partial \theta_n} & \cdots & \frac{\partial wrist_z}{\partial \theta_n} \end{pmatrix} \begin{pmatrix} \tau_1 \\ \vdots \\ \tau_n \end{pmatrix} \quad \text{(Equation 5)}$$

The Jacobian represents how much a small change in the net joint angles $\theta=(\theta_1, \ldots, \theta_n)$ will change the position of each of the n points. In Example 4, two points are considered—the elbow and the wrist—although it is possible to consider any number of points. For example, a point may be defined with respect to the instrument tip.

In Example 4, forces applied at the wrist are considered with respect to three directions, the cartesian directions x, y and z. The forces acting at a point can be considered with respect to any number of directions.

Each of the joints in the series of joints of the robot arm may be considered. Alternatively, a subset of the joints in the series of joints of the robot arm may be considered. For example, only the joints adjacent to each point (e.g. the wrist and the elbow) may be considered—or any number of joints either side of those points. A different subset of joints may be considered for each point. Practically, this can be achieved by setting entries in the Jacobian corresponding to joints not to be considered to zero.

In Example 4, the sensed torque state can be mapped to a selected torque state in the same manner as described with reference to Example 3. That is, sensed torque state is mapped to a selected torque state of a set of candidate torque states. The selected torque state is an element of the image of the Jacobian matrix shown in Equation 5. The selected torque state may be the torque state of the set of candidate torque states having the lowest Euclidian distance or least squares distance to the sensed torque state.

Having mapped the sensed torque state to a selected torque state, in step 503, the control system sends a command signal to the surgical robot arm to drive the robot arm such that the configuration of the robot arm is altered so as to comply with, compensate for, or conform with the selected torque state. For example, the torque data, $\tilde{\tau}_n$, relating to each joint in the selected torque state, z, may be used as an input to the mass-spring-damper model described with reference to FIG. 4 and Example 1.

Optionally, in Example 4, at least one force acting at each point may be determined by determining those forces corresponding to the selected torque state. In Example 4, one force acting at the elbow, $f_{elbow}$, and three forces acting at the wrist, $f_{wrist_x}$, $f_{wrist_y}$ and $f_{wrist_z}$, are determined. This can be achieved in a similar manner as described with reference to Example 3. That is, having mapped the sensed torque state to a selected torque state, this can be achieved by simply rearranging Equation 5 if the Jacobian matrix is invertible or using a function such as the Right inverse if the Jacobian is not invertible. Alternatively, a Moore-Penrose pseudoinverse of the Jacobian matrix can be used to map the sensed torque state to the selected torque state and determine the plurality of forces, $f_{elbow}$, $f_{wrist_x}$, $f_{wrist_y}$ and $f_{wrist_z}$, corresponding to the selected torque state in one step.

The control system may then send a command signal to the surgical robot arm to drive the robot arm such that the configuration of the robot arm is altered so as to comply with, compensate for, or conform with each of the determined forces. For example, the forces, $f_{elbow}$, $f_{wrist_x}$, $f_{wrist_y}$ and $f_{wrist_z}$ may be used as an input to the mass-spring-damper model described with reference to FIG. 4 and Example 2.

Optionally, after receiving the sensory data indicative of the torque state of the robot arm in step 501, the control system may determine, in dependence on an estimate of the current configuration of the robot arm, whether to control the configuration of the surgical robot arm to be altered in response to an externally applied force or torque in steps 502 and 503 in accordance with a force acting at: a single point of the robot arm determined in accordance with Example 3; or at least one force acting at each of the n points of the robot arm determined in accordance with Example 4); or by using a weighted combination of a force acting at a single point of the robot arm determined in accordance with Example 3 and a force acting at the same point of the n points of the robot arm determined in accordance with Example 4.

For example, when the Jacobian matrix used in Example 4 considers sensory data received from torque sensors at only a subset of the joints in the series of joints—such as those adjacent to a plurality of defined points—the accuracy with which the approach described with reference to Example 4 can resolve a force or torque applied at certain parts of the robot arm is reduced. If, for example, the control system is operating in a mode in which it is expected that an external force or torque will be applied at a certain part of the robot arm which cannot be accurately resolved using the approach described with reference to Example 4, the control system may determine to control the configuration of the surgical robot arm to be altered in response to an externally applied force or torque in accordance with a force acting at a single point of the robot arm (as described with reference to Example 3) and considering sensory data received from all of the torque sensors.

In another example, the configuration of the robot arm may be such that two or more of the directions being considered at the plurality of defined points become aligned (e.g. in Example 4, the direction considered at the elbow 304*d* and the one of x, y or z direction considered at the wrist joints 304*e-g*). This may be termed as a singular configuration of the robot arm. When the robot arm adopts a singular configuration, the accuracy with which either of the approaches described with reference to Examples 3 and 4 can resolve an applied force or torque acting at a point (e.g. such as the elbow) is reduced. Thus, in this scenario, the control system may estimate a force acting at a point (e.g. the elbow) of the robot arm using each of the approaches described with reference to Examples 3 and 4, and interpolate between those determined forces in order to determine a force acting at the elbow that will be used to control the configuration of the surgical robot arm. For example, Equation 6 may be used to interpolate between forces determined using each of the approaches described with reference to Examples 3 and 4.

$$f_{elbow} = (1-\beta)f_{elbow}^{Example\,3} + \beta f_{elbow}^{Example\,4} \quad \text{(Equation 6)}$$

Where β is a weighting value that varies with the determinant of the Jacobian matrix representing how much a small change in the net joint angles will change the position of each of the plurality of points (e.g. the Jacobian in Equation 5). The determinant of this Jacobian matrix can provide an estimate of the current configuration of the robot arm. For example, if the determinant of this Jacobian is below a threshold (e.g. closer to zero), the control system may apply a greater weight to the force determined to be acting at the point using the approach described with reference to Example 3. If the determinant of this Jacobian is above a threshold (e.g. further from zero), the control system may apply a greater weight to the force determined to be acting at the point using the approach described with reference to Example 4.

When the robot arm adopts a singular configuration, the control system may be further configured to consider a smaller subset of the joints in the series of joints of the robot arm using each of the approaches described with reference to Examples 3 and 4 before interpolating between the determined forces in accordance with Equation 6. The subset of the joints to be considered may depend on the nature of the singularity in the robot arm configuration and the point at which the force is to be resolved (e.g. joints nearby that point).

Optionally, the control system may determine that one or more torque sensors experience greater noise interference than others. In this scenario, the control system may assign more significance to the sensory data received from the sensors determined to experience less noise interference. In order to achieve this, the control system can apply a weighing value, $\alpha_1, \ldots, \alpha_n$, to the sensory data received from each torque sensor. For example, the inverse Jacobian matrix described in either Example 3 or 4 may be weighted by means of a diagonal matrix with the weights that correspond to each of the values of the torque state. That is, each weighting value $\alpha_n$ may be associated with the terms in the inverse Jacobian matrix relating to the change in angle $\theta_n$ of the joint $j_n$ to which the torque sensor providing the sensory data, is associated. In the examples where the Moore-Penrose pseudoinverse is used to map the sensed torque state to the selected torque state and determine the force corresponding to the selected torque state in one step, a diagonal weighting matrix encoding the weights to be applied to sensory data received from each torque sensor may be integrated within the Moore-Penrose pseudoinverse of the Jacobian matrix. The control system may determine the significance to be applied to each torque sensor such that the value of $$\sum_j \alpha_j^2(\tau_j - \bar{\tau}_j)^2$$

is minimised for $\alpha_1, \ldots, \alpha_n$, where $\alpha_n$ is a weighting value applied to the sensory data received from the $n^{th}$ torque sensor.

Surgical Mode

During the invasive procedure, the surgical robot arm may operate in the surgical mode. In the surgical mode, the surgical instrument is inside the patient's body. The control system commands the surgical robot arm such that its configuration can be altered in response to inputs received at a remote surgeon console (such as remote surgeon console 220 shown in FIG. 2). A surgeon may provide inputs to the remote console 220, e.g. via one or more surgeon input devices 223.

When operating in the surgical mode, the control system may cause certain parts of the robot arm to exhibit compliant-like behaviour—such as that described with reference to FIGS. 4 and 5. For example, the configuration of the elbow joint 304*d* may be capable of being altered in response to external forces in the manner described herein, so long as the position and orientation of the instrument 306 is not affected. Enabling such compliant-like behaviour whilst the robot arm is operating in the surgical mode allows, for example, a member of operating room staff to move the elbow of the robot arm so that they can access the patient during the procedure. Such compliant-like behaviour can also be a beneficial safety feature, for example, enabling the configuration of the robot arm to be altered when a member of the operating room staff "bumps" into the surgical robot arm.

In order to implement such compliant-like behaviour the control system may define an allowed area or volume for one or more parts the robot (e.g. the set of wrist joints 304*e-g*), such that the movement of those parts in response to an externally applied force or torque is confined within that allowed area or volume. The allowed area or volume is defined such that movements within that area or volume in response to an externally applied force or torque do not cause the position and orientation of the instrument 306 to be affected.

Referring back to step 401 of FIG. 4, in the surgical mode, the received sensory data may be indicative of a force or torque resulting from the effect of gravity on the part of the robot arm, any vibrations, inertia and/or accelerations at that part of the robot arm, a force or torque resulting from the externally applied force or torque at the part of the surgical robot arm, and further a force or torque at the part of the surgical robot arm resulting from the robot arm being driven by the control system in response to inputs received at the remote surgeon console. Thus, the sensory data may first be adjusted so as to discount the force or torque caused by the effect of gravity on the part of the robot arm, and/or any vibrations, inertia and/or accelerations at that part of the robot arm, and/or the force or torque at the part of the robot arm caused by the motors driving the robot arm in response to inputs received at a remote surgeon console. For example, the force or torque caused the effect of gravity on the part of the robot arm and the force or torque caused by the motors driving the robot arm in response to inputs received at a remote surgeon console may be subtracted from the sensory data.

Instrument Retract Mode

The instrument retract mode can be used in order to retract the instrument 306 from a patient's body. It can be desirable to retract the instrument form the patient's body after an invasive procedure has been completed. It can also be desirable to retract the instrument from the patient's body during the procedure. For example, it may be desirable to change or swap the instrument attached to the surgical robot arm during the invasive procedure. That is, it may be desirable to change the instrument in order to use a different instrument having different capabilities, or it may be desirable to change the instrument in the event that the instrument attached to the robot arm is faulty.

In the instrument retract mode, the control system may cause the surgical robot arm 301 to exhibit compliant-like behaviour—such as that described with reference to FIGS. 4 and 5. The control system may enable such compliant like behaviour so that a member of the operating room staff can retract the instrument from the patient's body. The control system may cause the configuration of the robot arm to be altered in response to an externally applied force or torque (e.g. a manual push or pull applied by a member of the operating room staff) so as to enable the instrument 306 to be retracted from patient's body along an axis parallel to the longitudinal axis of the instrument. With reference to FIG. 3, the longitudinal axis of the instrument 306 may be co-axial with the instrument shaft 361. That is, in the instrument retract mode, the control system may cause the configuration of the robot arm to be altered in response to external forces, but limit the freedom of motion of the robot arm such that the surgical instrument can only move linearly in directions parallel and/or co-axial with its longitudinal axis. The instrument 306 is retracted from patient's body along an axis parallel to the longitudinal axis of the instrument so as to minimise or negate damage or disruption to the surrounding tissues of the patient as the instrument is retracted.

Figure 7:
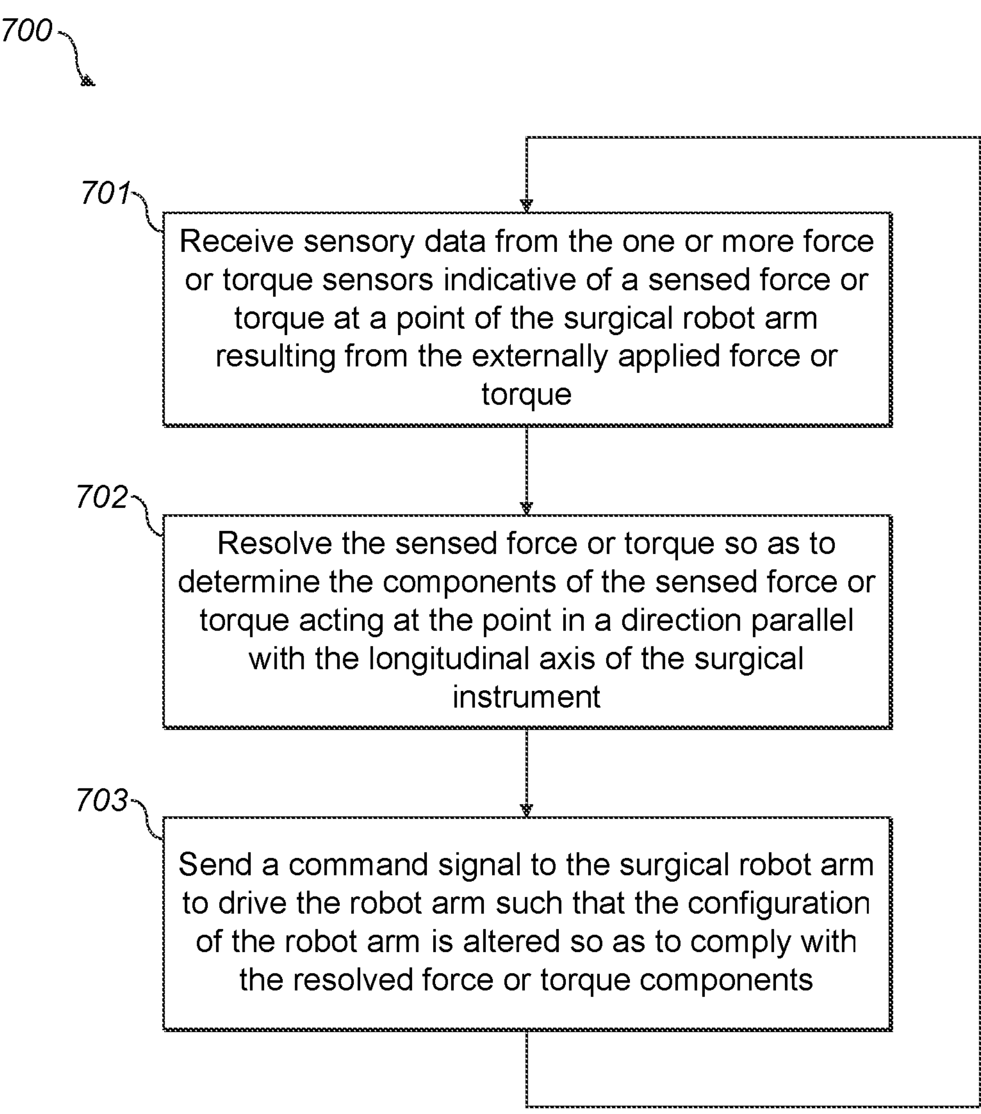
FIG. 7 is a flow diagram showing a control loop performed by a control system to alter the configuration of a surgical robot arm in response to an externally applied force or torque in an instrument retract mode.

FIG. 7 is a flow diagram showing a set of steps performed by a control system to alter the configuration of a surgical robot arm in response to an externally applied force in an instrument retract mode. The control system may be configured to perform multiple iterations of the set of steps shown in FIG. 7. That is, the control system may perform steps 701, 702 and 703 in sequence, followed by returning to step 701 to repeat that sequence. In other words, FIG. 7 is a flow diagram showing a control loop performed by a control system to alter the configuration of a surgical robot arm in response to an externally applied force or torque in the instrument retract mode.

On initialising the instrument retract mode, the control system may receive sensory data from one or more of position sensors 307*a-h* indicative of the rotational position one or more joints of the series of joints of the robot arm. Using that sensory data, the control system may determine the position of a point of the robot arm or of the instrument, and a direction parallel to the longitudinal axis of the surgical instrument that intersects the defined point. The point may be defined with respect to the distal end of the robot arm or with respect to the surgical instrument.

In step 701, the control system receives sensory data from the one or more force or torque sensors indicative of a sensed force or torque at the defined point resulting from the externally applied force or torque. As described herein, the received sensory data may in fact be indicative of a force or torque resulting from the effect of gravity on the defined point, and/or any vibrations, inertia and/or accelerations at that defined point, as well as a force or torque resulting from the externally applied force or torque at the defined point. Thus, the sensory data may first be adjusted for the force or torque caused the effect of gravity of the robot arm, and/or any vibrations, inertia and/or accelerations at that part of the robot arm.

In step 702, the control system resolves the sensed force or torque so as to determine the components of the sensed force or torque acting in the direction parallel with the longitudinal axis of a surgical instrument attached to the attachment.

In examples where the instrument extends along an axis coincident with the rotation axis of joint 304*g*, the control system may use the sensory data to determine if an applied external force is coincident (and therefore also inherently parallel) with the longitudinal axis of the instrument. In examples where the instrument extends linearly parallel with the rotation axis of the terminal joint 304*g* of the robot arm (but not necessarily co-axial with that rotation axis), the control system may use the sensory data to determine if an applied external force is parallel with the longitudinal axis of the instrument.

In order to resolve the sensed force or torque, the control system may implement a method similar to that described with reference to FIG. 5. That is, the sensory data may be received from one or more torque sensors and be indicative of a sensed torque state at the defined point resulting from the externally applied force or torque. The control system may then resolve the sensed toque state by mapping the sensed torque state to a selected torque state of a set of candidate torque states. As described with reference to FIG. 5, each torque state in the set of candidate torque states may be an element of the image of a Jacobian matrix. Having mapped the sensed torque state to a selected torque state, the control system may determine the corresponding force indicative of a force acting at the defined point and in a direction parallel to the longitudinal axis of the surgical instrument as a result of the externally applied force or torque. In the instrument retract mode, the control system may be configured to multiply the Jacobian matrix by a column vector representing the direction of the axis parallel with the longitudinal axis of the surgical instrument such that the one or more forces from which the corresponding force is determined consist of (e.g. comprise only) forces acting along the axis parallel with the longitudinal axis of the surgical instrument. Example 5 is a detailed example illustrating how step 702 may be performed.

Example 5

In Example 5, a point, p, is defined with respect to the robot arm or with respect to the instrument. For an external force, f, applied at p it is possible to deduce the force f acting in the direction, $\hat{d}$, parallel to the longitudinal axis of the instrument axis by applying the principle of virtual work to the net joint torques, τ. This information can be encoded in the Jacobian, $J_{p,\hat{d}}$ in accordance with:

(Equation 7)

$$\tau = \begin{pmatrix} \tau_1 \\ \vdots \\ \tau_n \end{pmatrix} = \begin{pmatrix} \frac{\partial p_x}{\partial \theta_1} & \cdots & \frac{\partial p_z}{\partial \theta_1} \\ \vdots & \ddots & \vdots \\ \frac{\partial p_x}{\partial \theta_n} & \cdots & \frac{\partial p_z}{\partial \theta_n} \end{pmatrix} \begin{pmatrix} \hat{d}_x \\ \hat{d}_y \\ \hat{d}_z \end{pmatrix} f = J_p \hat{d} f = \begin{pmatrix} \frac{\partial p_{\hat{d}}}{\partial \theta_1} \\ \vdots \\ \frac{\partial p_{\hat{d}}}{\partial \theta_n} \end{pmatrix} f = J_{p,\hat{d}} f.$$

where direction, $\hat{d}$, is a unit vector having the components ($\hat{d}_x$, $\hat{d}_y$, $\hat{d}_z$) and $J_{p,\hat{d}}=J_p\ \hat{d}$ is a 1 by n Jacobian matrix represents how much a small change in the net joint angles $\theta=(\theta_1, \ldots, \theta_n)$ will move the point, p, in direction, $\hat{d}$. The force, f, can be determined using the sensed torque, τ, in accordance with the expression $\tau=J_{p,\hat{d}}\ f$ using any of the methods described with reference to FIG. 5 and Example 3. As the Jacobian matrix has been multiplied by column vector $\hat{d}$, representing the direction of the axis parallel with the longitudinal axis of the surgical instrument, the one or more forces from which the force, f, corresponding to the torque state is determined consist of (e.g. comprise only) forces acting along the axis parallel with the longitudinal axis of the surgical instrument.

Returning to FIG. 7, in step 703, a command signal is sent to the surgical robot arm to drive the robot arm such that the configuration of the robot arm is altered so as to comply with, compensate for, or conform with the resolved force or torque components. For example, a force, f, determined in accordance with Example 5 may be used as an input to the mass-spring-damper model described with reference to FIG. 4 and Example 2 so as to determine how the configuration of the surgical robot arm should be altered. As the force, f, includes only the components of the applied force or torque acting at the defined point and in a direction parallel with the longitudinal axis of the surgical instrument, the position to which the defined point is to be driven determined in accordance with Example 2 will be on the direction parallel with the longitudinal axis of the surgical instrument.

In other modes (not described in detail herein), forces may be resolved in accordance with the principles described with reference to FIG. 7 for one or more different directions (e.g. a direction perpendicular to the axis of the instrument shaft).

The control system may be further configured to define a stop position in dependence on the defined position on the robot arm or instrument. The stop position may be a position on the direction parallel to the longitudinal axis of the surgical instrument at which the control system does not permit the defined point to be driven further towards the patient. The definition of a stop position prevents the operator of the surgical robot arm (e.g. the member of bedside staff) pushing the instrument (e.g. the instrument being retracted, or a new instrument which has been swapped for the retracted instrument) too far into the patient's body. This can prevent damage to the patient.

The control system may optionally notify the operator (e.g. the member of bedside staff) of the surgical robot arm if it determines that the surgical instrument cannot be fully retracted from the patient. The control system may determine using data from the position sensors 307*a-h* that the current angular position of one or more of the joints is too close to the end of their range of travel to permit the instrument to be retracted from the patient's body. The control system may make this determination when the instrument retract mode is initialised, or during use of the instrument retract mode. If the surgical instrument cannot be fully retracted from the patient using the instrument retract mode, the control system may automatically cause the position of one or more of the joints of the surgical robot arm to be adjusted to the centre of their range of travel—in such a way that the position and orientation of the instrument is unchanged—or, the control system may cause the surgical robot arm to operate in the surgical mode so that the one or more joints can be adjusted in response to inputs received at a remote surgeon console (such as remote surgeon console 220 shown in FIG. 2).

The control system may optionally enable the instrument and/or the instrument attachment to be rotatable when in the instrument retract mode. That is, the control system may enable the joint of the series of joints that has a rotation axis parallel with the longitudinal axis of the instrument, e.g. joint 304*g*, to rotate as the instrument is being retracted. This rotational freedom can aid the member of operating room staff in removing or changing the instrument. For example, it may be desirable for the operator to be able to rotate the instrument so as to dislodge an obstruction to the end effector as the instrument is being retracted from the patient, or it may be desirable for the operator to be able to rotate the instrument attachment so as to make it easier to change the instrument for an alternative instrument.

In order to achieve this, the control system may also perform the method described with reference to FIG. 4 and Example 1 in order to control the angular displacement of a joint, e.g. joint 304*g*. The control system may perform this method independently of (e.g. separately to, but concurrently with) controlling the linear displacement of a defined point along the direction parallel with the longitudinal axis of the instrument. This may be particularly suitable where the joint (e.g. joint 304*g*) is located more distally than the defined point. This is because a change in the angular position of that joint would not cause a displacement or change of orientation of the defined point.

For example, the control system may be further configured to receive sensory data from a force or torque sensor indicative of a sensed force or torque at a revolute joint of the series of joints resulting from the externally applied force or torque, the rotational axis of the revolute joint being parallel with the longitudinal axis of the surgical instrument. Optionally, the control system may process received torque values in accordance with the method described with reference to FIG. 5. The control system may then determine an angular position of the revolute joint using a reference angular position, whereby the sensed force or torque is compensated by moving the revolute joint to the determined angular position. The reference angular position is the angular position to which the control system is configured to cause the revolute joint to be driven when no external force is sensed at the revolute joint. The control system may use a mass-spring-damper model as described with reference to Example 1 to determine the angular position. The control system may use a mass-spring-damper model as described with reference to Example 1 to determine the velocity and acceleration with which the joint is to be moved to that position. The control system may be configured to send a command signal to the surgical robot arm to drive the revolute joint to the determined angular position. "Elastic" and "plastic" behaviour of the revolute joint can be implemented as described herein with reference to FIG. 4.

The robot arm described herein could be for purposes other than surgery. For example, the port could be an inspection port in a manufactured article such as a car engine and the robot could control a viewing instrument for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control system of a surgical robot arm, the surgical robot arm comprising a series of joints by which the configuration of that surgical robot arm can be altered and one or more force or torque sensors, each force or torque sensor configured to sense a force or torque at a joint of the series of joints, the control system being configured to cause the robot arm to operate in:

a compliant mode in which the control system is configured to control the configuration of the surgical robot arm to be altered in response to an externally applied force or torque by:

receiving sensory data from the one or more force or torque sensors indicative of a sensed force or torque at a part of the surgical robot arm resulting from the externally applied force or torque;

determining a position of the part of the surgical robot arm using a reference position, whereby the sensed force or torque would be compensated by moving the part of the surgical robot arm to the determined position;

sending a command signal to the surgical robot arm to drive the part of the surgical robot arm to the determined position; and updating the reference position if the difference between the reference position and the determined position is greater than a threshold displacement such that the control system is configured to control the configuration of the surgical robot arm:

to have elastic behavior, in which the robot arm is displaced from a position in response to the externally applied force or torque, but returns to that position when the externally applied force or torque is no longer being applied, if the difference between the reference position and the determined position is less than the threshold displacement; and to have plastic behavior, in which the robot arm is displaced to a position in response to the externally applied force or torque, and retains that position even when the externally applied force or torque is no longer being applied, if the difference between the reference position and the determined position is greater than a threshold displacement; and a surgical mode in which the control system is configured to control the configuration of the surgical robot arm to be altered in response to inputs receiving at a remote surgeon console, the remote surgeon console being configured to receive inputs from a surgeon via one or more surgeon input devices so as to enable the surgeon to control the surgical robot arm to perform surgery.

2. The control system as claimed in claim 1, the control system being further configured to iteratively perform a control loop comprising the receiving, determining, sending and updating steps.

3. The control system as claimed in claim 2, the control system being further configured to maintain, for a subsequent iteration, the reference position used in the determining step of the present iteration if the difference between the reference position and the determined position is less than the threshold displacement.

4. The control system as claimed in claim 1, wherein the reference position is the position to which the control system is configured to cause the part of the surgical robot arm to be driven when sensory data is received from the one or more force or torque sensors indicative of no external force or torque acting at the part.

5. The control system as claimed in claim 1, wherein determining the position of the part of the surgical robot arm using the reference position comprises determining a position that satisfies a mass-spring-damper model having a position term that depends on the reference position and the determined position.

6. The control system as claimed in claim 5, wherein the mass-spring-damper model takes the form, $M\ddot{P}+D\dot{P}+K(P-P_{ref})=-X$, where P is the determined position, $P_{ref}$ is the reference position, X is the sensed force or torque at the part of the surgical robot arm and M, D and K are constants.

7. The control system as claimed in claim 1, the surgical robot arm further comprising an attachment for a surgical instrument at a distal end of the robot arm, wherein the control system is configured to cause the robot arm to operate in:

the surgical mode in which a surgical instrument attached to the attachment is inside a patient's body; and an instrument retract mode in which the surgical instrument is retracted from the patient's body in response to the externally applied force or torque.

8. The control system as claimed in claim 7, wherein the part of the robot arm is a point defined with respect to the distal end of the robot arm or a point defined with respect to the surgical instrument.

9. The control system as claimed in claim 8, wherein the sensory data is received from two or more force or torque sensors and is indicative of sensed forces or torques at two or more joints of the series of joints resulting from the externally applied force or torque, and the control system is further configured to:

resolve said sensory data so as to determine the force or torque at the defined point resulting from the externally applied force or torque.

10. The control system as claimed in claim 8, the control system being further configured to, in the instrument retract mode:

resolve the sensory data so as to determine the components of the sensed force or torque parallel with the longitudinal axis of the surgical instrument attached to the attachment; and determining the position of the defined point of the surgical robot arm using the reference position, whereby only the resolved components of the sensed force or torque would be compensated by moving the point of the surgical robot arm to the determined position, such that the determined position is constrained to be on the axis parallel with the longitudinal axis of the surgical instrument.

11. The control system as claimed in claim 10, wherein the threshold displacement is a linear displacement along the axis parallel with the longitudinal axis of the surgical instrument.

12. The control system as claimed in claim 10, the control system being further configured to control the configuration of the surgical robot arm to be altered in response to an externally applied force or torque by:

receiving sensory data from a force or torque sensor indicative of a sensed force or torque at a revolute joint of the series of joints resulting from the externally applied force or torque, the rotational axis of the revolute joint being parallel with the longitudinal axis of the surgical instrument;

determining an angular position of the revolute joint using a reference angular position, whereby the sensed force or torque would be compensated by moving the revolute joint to the determined angular position;

sending a command signal to the surgical robot arm to drive the revolute joint to the determined angular position; and updating the reference angular position if the difference between the reference angular position and the determined angular position is greater than a threshold displacement.

13. The control system as claimed in claim 12, the control system being further configured to iteratively perform a control loop comprising the receiving, determining, sending and updating steps of claim 12.

14. The control system as claimed in claim 13, the control system being further configured to maintain, for a subsequent iteration, the reference angular position used in the determining step of the present iteration if the difference between the reference angular position and the determined angular position is less than the threshold displacement.

15. The control system as claimed in claim 12, wherein the reference angular position is the angular position to which the control system is configured to cause the revolute joint to be driven when no external force is sensed at the revolute joint.

16. The control system as claimed in claim 12, wherein determining the angular position of the revolute joint using the reference angular position comprises determining an angular position that satisfies a mass-spring-damper model having a position term that depends on the reference angular position and the determined angular position.

17. The control system as claimed in claim 16, wherein the mass-spring-damper model takes the form, $M\ddot{\theta}+D\dot{\theta}+K(\theta-\theta_{ref})=-X$, where $\theta$ is the determined angular position, $\theta_{ref}$ is the reference angular position, X is the sensed force or torque at the revolute joint of the surgical robot arm and M, D and K are constants.

18. The control system as claimed in claim 1, wherein the part of the surgical robot arm is a joint of the series of joints and the threshold displacement is an angular displacement of the joint.

19. The control system as claimed in claim 1, wherein the surgical robot arm further comprises one or more motors, each motor being configured to drive a joint of the series of joints in response to the command signal sent by the control system.

20. A method of controlling a surgical robot arm, the surgical robot arm comprising a series of joints by which the configuration of that surgical robot arm can be altered and one or more force or torque sensors, each force or torque sensor configured to sense a force or torque at a joint of the series of joints, the method comprising causing the robot arm to operate in:

a compliant mode by controlling the configuration of the surgical robot arm to be altered in response to an externally applied force or torque by:

receiving sensory data from the one or more force or torque sensors indicative of a sensed force or torque at a part of the surgical robot arm resulting from the externally applied force or torque;

determining a position of the part of the surgical robot arm using a reference position, whereby the sensed force or torque would be compensated by moving the part of the surgical robot arm to the determined position;

sending a command signal to the surgical robot arm to drive the part of the surgical robot arm to the determined position; and updating the reference position if the difference between the reference position and the determined position is greater than a threshold displacement such that the control system controls the configuration of the surgical robot arm:

to have elastic behaviour, in which the robot arm is displaced from a position in response to the externally applied force or torque, but returns to that position when the externally applied force or torque is no longer being applied, if the difference between the reference position and the determined position is less than the threshold displacement; and to have plastic behaviour, in which the robot arm is displaced to a position in response to the externally applied force or torque, and retains that position even when the externally applied force or torque is no longer being applied, if the difference between the reference position and the determined position is greater than a threshold displacement; and a surgical mode by controlling the configuration of the surgical robot arm to be altered in response to inputs received at a remote surgeon console, the remote surgeon console being configured to receive inputs from a surgeon via one or more surgeon input devices so as to enable the surgeon to control the surgical robot arm to perform surgery.

* * * * *